United States Patent [19]

Rose, Jr.

[11] Patent Number: 5,282,941
[45] Date of Patent: Feb. 1, 1994

[54] CAPILLARY GEL ELECTROPHORESIS COLUMNS AND METHOD OF PREPARING THE SAME

[75] Inventor: Donald J. Rose, Jr., Mountain View, Calif.

[73] Assignee: Hewlett-Packard Company, Palo Alto, Calif.

[21] Appl. No.: 914,232

[22] Filed: Jul. 13, 1992

Related U.S. Application Data

[63] Continuation of Ser. No. 628,278, Dec. 14, 1990, abandoned.

[51] Int. Cl.$^5$ .................. G01N 27/26; G01N 27/447
[52] U.S. Cl. .................. 204/182.8; 204/299 R; 204/180.1
[58] Field of Search .............. 204/299 R, 182.8, 180.1

[56] References Cited

U.S. PATENT DOCUMENTS

| | | | |
|---|---|---|---|
| 4,690,749 | 9/1987 | Van Alstin et al. | 204/299 R |
| 4,865,707 | 9/1989 | Karger et al. | 204/299 R X |
| 4,997,537 | 3/1991 | Karger et al. | 204/299 R X |
| 5,141,612 | 8/1992 | Schomburg et al. | 204/180.1 X |

*Primary Examiner*—John Niebling
*Assistant Examiner*—John S. Starsiak, Jr.

[57] ABSTRACT

Capillary tubes useful for performing capillary zone electrophoresis separation techniques are prepared by first forming a matrix of hydrophilic molecules which is thereafter incorporated into an electrophoretic gel. The analytical media exhibits strong structural integrity, uniformity, and adheres well to the capillary tubes.

48 Claims, 4 Drawing Sheets

CAPILLARY GEL ELECTROPHORESIS COLUMNS AND METHOD OF PREPARING THE SAME

This is a continuation of copending application Ser. No. 07/628,278 filed on Dec. 14, 1990, now abandoned.

FIELD OF THE INVENTION

The present invention relates generally to gel electrophoresis and more particularly to gel-containing microcapillary columns for high performance analytical electrophoresis that are substantially free of shrinkage defects and a method for making such devices.

BACKGROUND OF THE INVENTION

In electrophoresis, an ionic sample is placed at one end of the column. The ionized components migrate differentially according to charge and bulk under the influence of an axially applied electric field. After a predetermined time, the electric field is removed and the components analyzed according to axial position along the tube.

Capillary zone electrophoresis has proven useful as an efficient method for the separation of certain small solutes. Attractive factors for CZE include the small sample sizes, little or no sample pretreatment, high solution, automation, and the potential for quantification and recovery of biologically-active samples. Detection and quantitation of the migrating ions can be carried out by measuring, for example, UV absorbance at a particular wavelength. Collection can be made directly into any conducting solution. Microcapillary gel electrophoresis is particularly wellsuited for separating proteins and other biopolymers. Very high efficiency and resolving power are possible with capillary gel columns, permitting rapid separation of biopolymers.

The columns of gel can be prepared by filling a tube with an aqueous mixture of acrylamide monomer, and then polymerizing the monomer. In the case of acrylamide, as is generally true in polymer chemistry, the polymer is substantially denser than the original prepolymer, e.g., the monomer, dimer, or oligomer, from which the polymer is formed. Accordingly, significant shrinkage occurs during polymerization. Besides crosslinked polyacrylamide gels, agarose is often employed as the medium in gel electrophoresis, especially for separation by molecular weight of large macromolecules such as nucleic acids. Agarose is a natural polysaccharide isolated from agar and agarose gel is a relatively transparent anticonvection medium that prevents broadening of the zones during separation. However, as in the formation of polyacrylamide gels, agarose gels are also adversely affected by shrinkage during polymerization.

As a consequence of this shrinkage, the forming gel has a tendency to pull away from the interior walls of the tube. The voids thus formed between the tube and the gel can disturb the uniformity of an applied electric field, seriously diminish the resolution of the electrophoresis process, and cause local heating. Moreover, the separation of the gel from the tube aggravates a tendency of the gel to migrate out of the tube during electrophoresis. Furthermore, the gel is not homogeneous, in terms of pore size, both radially (center to wall) and longitudinally (end to end).

One common approach with regard to the problem of maintaining the structural integrity of the gel during electrophoresis has been to coat the interior of the tube with a bonding agent which forms covalent bonds between the surface of the tube and the polymer chains. In these microcolumns, a bifunctional silane, for instance, is used as a bonding agent such that one functionality reacts with the inner surface of the capillary and the other (acrylic) functionality reacts with the polymerizing acrylamide monomer network, thus immobilizing the gel matrix. Although separation and resulting migration are mitigated, the tension introduced by the tendency of the gel to shrink during polymerization causes bubble-like voids within the gel itself. This adversely affects the gel's uniformity. These internal voids also distort the applied electric field and diminish the resolution of the electrophoresis process. See Karger et al., U.S. Pat. No. 4,865,706.

In a modification of the above approach, microcapillaries are prepared in which the polymeric gel contains hydrophilic polymers. However, the use of the hydrophilic polymer often leads to polymeric gels that are not sufficiently transparent because of phase separation during polymerization. See Karger et al., U.S. Pat. No. 4,865,707, issued Sep. 12, 1989.

The problem of shrinkage has been addressed and partially solved by pressurizing the monomer to its final polymer volume. See Bente, III et al., U.S. Pat. No. 4,810,456, issued Mar. 7, 1989. Use of pressure polymerization results in a fairly homogenous gel (as viewed under a microscope) but the gel develops "air cores" when it is exposed to a moderate electric field (100 V/cm). It is believed that the inhomogeneities which form during polymerization under pressure are caused by the rapid initiation of polymerization of the reaction due to the more reactive, vis-a-vis acrylamide, acrylic functional group near the wall surface. As the polymerization reaction progresses towards the center of the capillary, acrylamide monomer concentration in the middle of the capillary is decreased, resulting in an inhomogeneous gel.

SUMMARY OF THE INVENTION

It is an object of the present invention to provide capillary tubes with gel based media that are useful for electrophoretic separations of solutes and in which the medium substantially adheres to the surface of the tubes.

It is another object of the present invention to provide gel containing capillary tubes in which the gel is homogenous throughout the entire cross section of the capillary. Other objects and advantages of the invention will be apparent to those skilled in the art to which the invention pertains.

These and other objects are accomplished by the inventive device and method in which the inner surface of a microcapillary is first modified prior to the formation of electrophoretic gel. Specifically, a matrix or network of hydrophilic molecules that are covalently bonded to a substantial portion of the inner surface is prepared. Thereafter, the matrix is brought into intimate contact with the appropriate gel-forming monomer and crosslinker solution. Upon polymerization of the solution, the matrix becomes enmeshed or embedded into the gel. The matrix molecules can be of any configuration, and the matrix molecules need not be covalently bonded to the gel molecules. Rather, incorporation of the matrix into the gel is established primarily through hydrogen bonding, dipole-dipole interaction, Van der Waal's forces, and other non-covalent intermolecular forces. However, in some embodiments of the invention, there may be covalent bonding between molecules of the matrix and molecules of the polymeric gel.

The interaction between the matrix and polymeric gel significantly reduces the effect of shrinkage normally encountered during polymerization. Moreover, it is believed that the matrix contains sites for immobilization which have the same reactivity as the gel polymerization reaction. It is believed that this results in a gel polymerization reaction that proceeds at a relatively constant rate over the entire cross-section of the capillary to form a homogeneous gel.

In one preferred embodiment of the invention, the internal surface of a fused-silica microcapillary is brought into contact with an acrylic silane. The silanol groups of the capillary surface thereupon react with the acrylic silane to form linear molecules that are covalently bonded to the surface with each molecule having a terminal double bond. Thereafter, the capillaries are filled with N,N'-methylenebisacrylamide and polymerization results in the coupling of the N,N'-methylenebisacrylamide to the linear molecules that are covalently bonded to the surface of capillary. Moreover, the N,N'-methylenebisacrylamide will crosslink to form a branch polymer matrix which contains reactive double bonds at the end of each polymer chain. Finally, the capillary is filled with the appropriate amount of an acrylamide/N,N'-methylenebisacrylamide solution, which is thereafter polymerized to form the inventive polymeric gel with the matrix embedded therein.

DETAILED DESCRIPTION OF THE PREFERRED EMBODIMENT

General Description

The inventive device comprises a gel-containing microcolumn suitable for high performance analytical electrophoresis in which the gel is uniformly distributed within the microcolumn bore and the gel remains stationary within the capillary under the influence of the high electric field. The homogeneity and structural integrity of the gel are achieved in part by first forming a matrix (or network) of hydrophilic molecules that is covalently bonded to a substantial portion of the inner surface of the capillary. Once the matrix is in place, the capillary is filled with any appropriate gel forming monomer and crosslinker solution. Preferably, the matrix is in intimate contact with the solution. After polymerization, the gel which forms has the matrix incorporated or embedded therein. The molecules of the matrix can be of any configuration, namely linear, branched, crosslinked, or any combination thereof. The primary criteria are that the matrix molecules be generally compatible with the gel (e.g., hydrophilic) and that they can be readily incorporated into the gel. The matrix molecules need not be covalently bonded to the gel molecules, rather, incorporation of the matrix into the gel is through hydrogen bonding, dipole-dipole interaction, Van der Waals forces, and other non-covalent intermolecular forces. However, in one embodiment of the invention, some of the molecules of the matrix can contain reactive groups (or active sites) that will react with and bond to molecules of the polymeric gel.

Figure 1A:
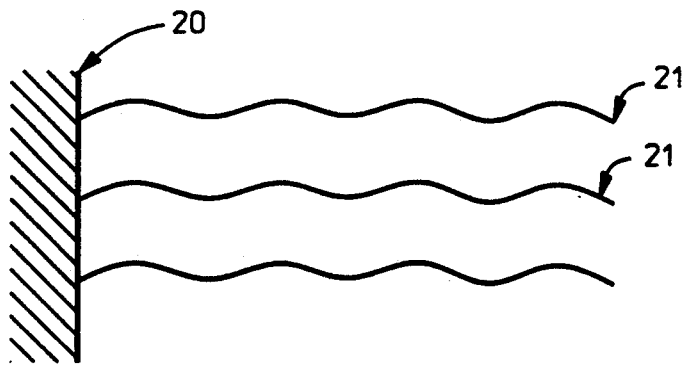
FIG. 1(a)-(b) depict four inventive matrix embodiments.
Figure 1B:
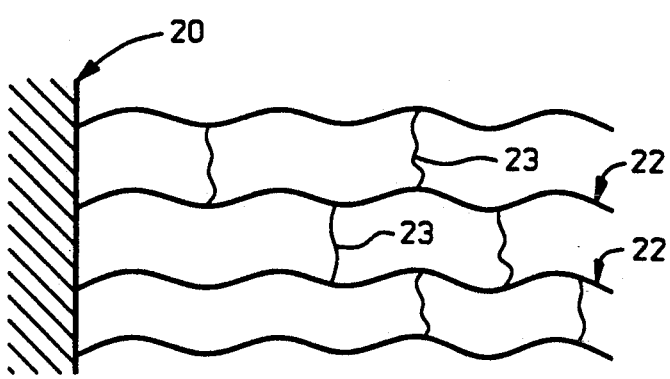
Figure 1C:
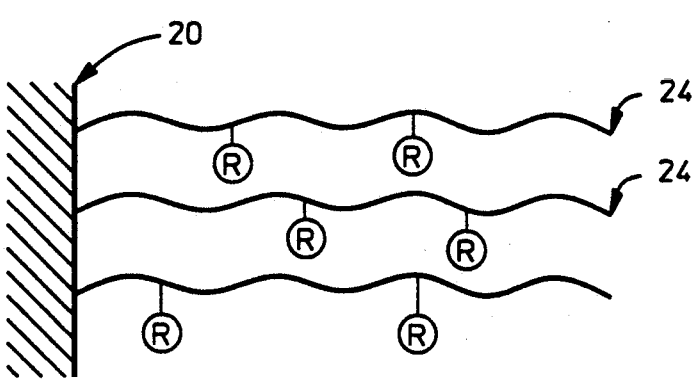
Figure 1D:
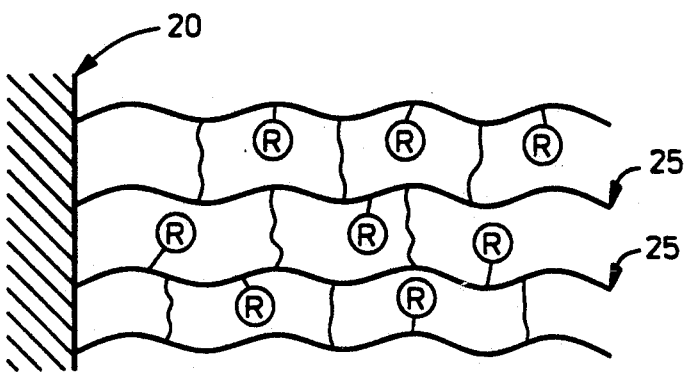

FIGS. 1(a)-(b) illustrate four embodiments of the matrix. In each figure, the matrix is covalently bonded to the microcapillary inner surface 20. In FIG. 1(a), the matrix comprises linear, unbranched hydrophilic molecules 21. In FIG. 1(b), the matrix comprises linear hydrophilic molecules 22 that are interconnected by crosslinking reagent molecules 23. In FIG. 1(c), the matrix comprises linear hydrophiic molecules 24 that contain reactive sites that are designated as ®. Finally, in FIG. 1(d), the matrix comprises cross-linked hydrophilic molecules 25 with reactive sites ®. Although not shown, in each of the embodiments depicted in FIGS. 1(c)-(b), the hydrophilic molecules can also comprise side chains attached thereto.

The inventive gel-filled capillary contains gel which is homogenous, in terms of pore size, both radially (centered to wall) and longitudinally (end to end of capillary). Moreover, the adverse effects of gel shrinkage are significantly reduced.

DESCRIPTION OF DEVICE AND PROCESS

Figure 2:
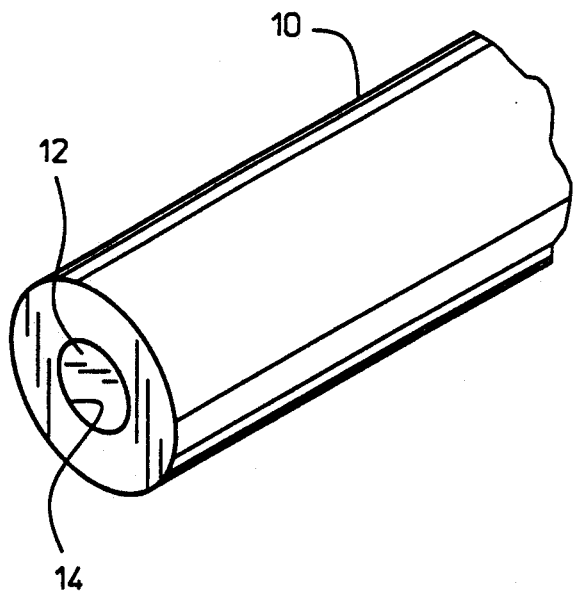
FIG. 2 shows a magnified perspective view of the end of the gel-containing microcapillary of the invention.

As shown in FIG. 2, the inventive device includes a microcapillary 10, a polymeric gel material 12 within the bore of this microcapillary 10, and a matrix (not shown) which is covalently bonded to the inner surface 14 of the microcapillary and which is embedded in the gel. The microcapillary 10 of the present invention can be made of any suitable material provided that the detection system to be employed in the electrophoresis can function adequately with the microcapillary material. A preferred material is fused-silica.

Although the invention is not limited by the dimensions of the microcapillary, the dimensions are important in two respects. First, as the internal diameter of the microcapillary is reduced, the electric current and the resultant heating is reduced. Second, the thinner the capillary wall can be made, the better heat transfer from the microcapillary is achieved. Thus, it is desirable that the microcapillary have a minimum internal diameter and also a minimum wall thickness. Capillaries having an internal diameter range from 10 to 200 μm and a wall thickness range less than approximately 40 μm function well. A preferred range of internal diameters is 25 to 100 μm and a preferred range of wall thickness is 25 to 35 μm. A polyimide (or other suitable polymer) coating on the microcapillary permits easy handling of thin-walled capillaries.

The polymeric gel material employed can be any polymer which is suitable for electrophoresis. Normally, polymers will have a pore structure which can be varied by varying the amounts of monomer and the reaction conditions employed. Preferred polymeric gels are crosslinked polymers wherein crosslinking agents are added to the monomer solution before polymerization. Examples of such polymeric systems are polyacrylamide and mixtures of agarose and polyacrylamide. A preferred polymeric gel material is based on acrylamide and N,N'-methylenebisacrylamide, the N,N'-methylenebisacrylamide serving as a crosslinking agent. Other possible crosslinking agents are N,N'-(1,2-dihydroxyethylene)bisacrylamide, N,N'-diallyltartardiamide, and N,N'-cystamine-bisacrylamide.

Agarose is often the medium of choice for the separation by molecular weight of large macromolecules ($\geqq 500,000$ daltons). For example, agarose is a preferred gel matrix for resolving nucleic acids. Sieving in agarose is dependent on gel concentration and can therefore be increased by increasing the percentage of agarose in the gel. Derivatization of agarose, e.g., by hydroxyethylation, has been observed to increase the sieving properties of these gels. Moreover, various additives may be included in agarose to modify the properties of the matrix. For example, polyols can be used to increase mechanical stability, probably by increased hydrogen bonding, in the gelled media and to assist in adhesiveness. Illustrative polyols used for this purpose include sorbitol, sucrose, erythritol, and polyethylene glycol. Appropriate amounts of such additional components are in a range from about 0.5% to 10%.

The matrix comprises hydrophilic molecules that are covalently bonded to the capillary wall. These molecules may be linear, branched, or a mixture of both, and the molecules may also contain functional groups (reactive sites) that react with and bond to molecules of the gel. Regardless of the particular form of the matrix, the matrix can be analogized to a set of "entangling fingers" that are embedded in the polymeric gel. The presence of the matrix during the polymerization of the monomer solution which forms the gel greatly reduces shrinkage and other mechanical problems associated with gel formation. As will be further discussed, it is believed that in certain embodiments of the invention, the matrix contains sites for immobilization which have the same reactivity as the gel polymerization reaction. It is believed that this permits the polymerization reaction to proceed at the same rate over the entire cross-section of the capillary to form a homogenous gel.

Figure 3:
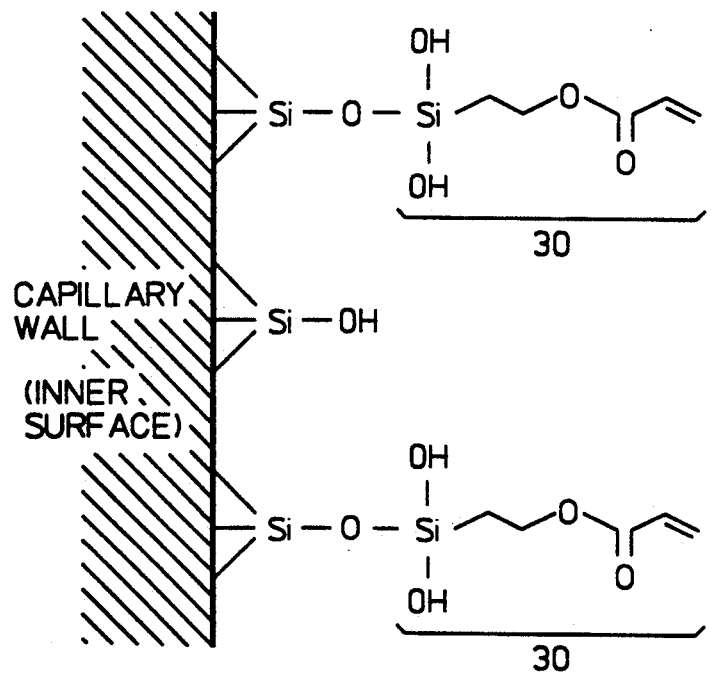
FIG. 3 depicts linear molecules formed by the reaction of acrylic silane molecules with the silanol groups of the capillary surface.

The preparation of a preferred embodiment of the gel-containing microcapillary of the present invention comprising a cross-linked matrix is as follows. First, the internal surface of a fused-silica microcapillary is brought into contact with an acrylic silane such as acryloxypropyltrichlorisilane. The silanol groups of the capillary surface will react with the acrylic silane to form molecules covalently bonded to the surface with each molecule having a terminal double bond. The modified capillary surface with the linear molecules 30 attached thereto is shown in FIG. 3.

Figure 4:
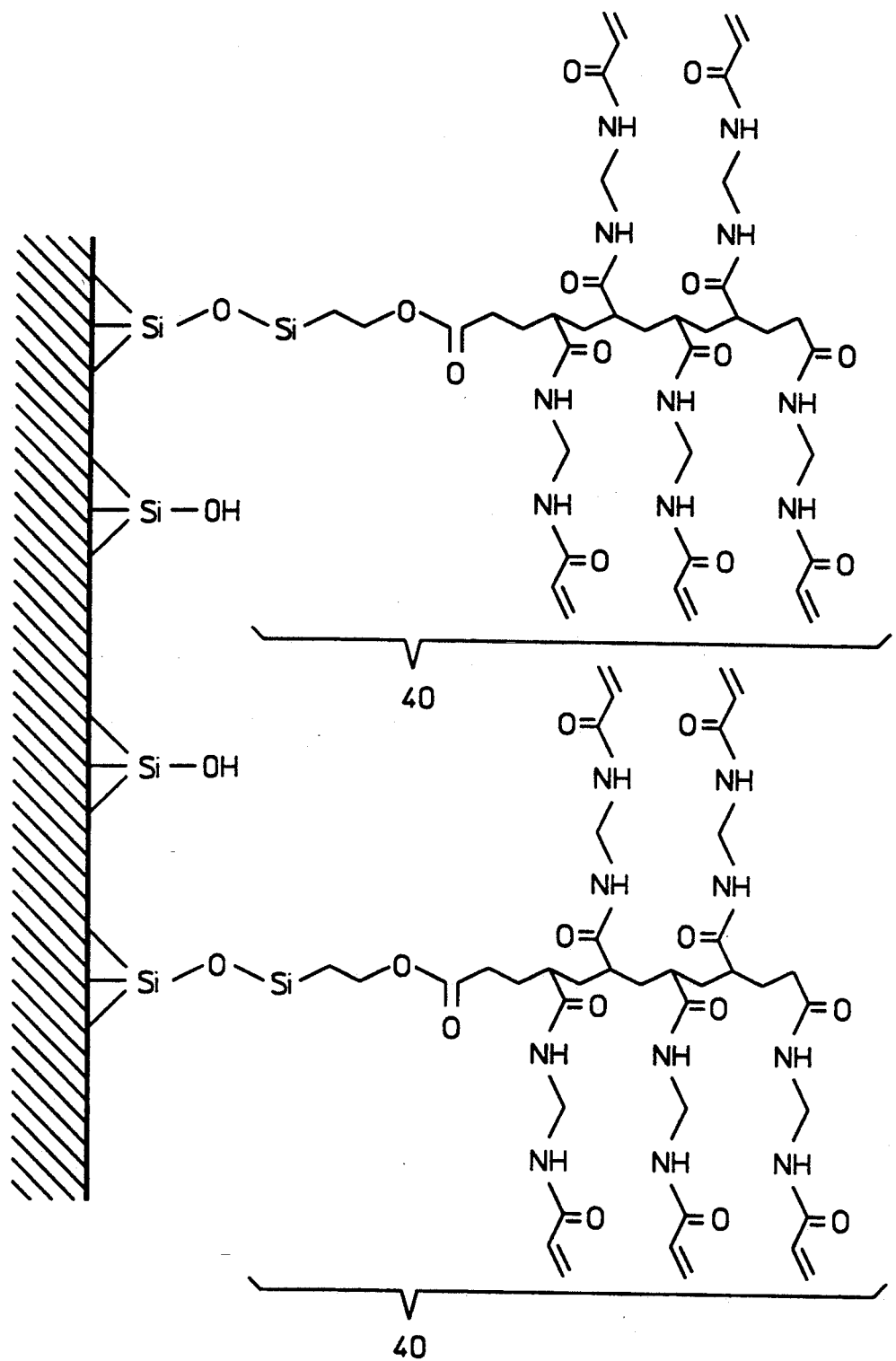
FIG. 4 depicts a crosslinked branched polymer matrix.

Next, if necessary, the capillary bore is flushed to remove any unreacted acrylic silane, and thereafter the capillary is filled with N,N'-methylenebisacrylamide. Appropriate catalysts are then added to initiate a reaction in which the N,N'-methylenebisacrylamide is coupled to the linear molecules 30. The polymerization reaction is preferably initiated with ammonium persulfate and N,N,N',N'-tetramethyleneethylenediamine, although other free radical polymerization initiators may be employed as known by those skilled in the art. In addition, the N,N'-methylenebisacrylamide will crosslink to form a branch polymer matrix or network 40 comprising of reactive double bonds at the end of each polymer chain as shown in FIG. 4. It is believed that by treating the modified "acrylic" surface with N,N'-methylenebisacrylamide, sites for immobilization having the same reactivity as gel polymerization are formed. Thus the gel polymerization reaction proceeds at the same rate over the entire cross-sectional of the capillary to form a homogenous gel. If necessary, the system is thereafter flushed with water to remove unreacted N,N'-methylenebisacrylamide and then purged with air. The oxygen quenches the reaction.

Finally, the capillary is filled with appropriate amounts of an acrylamide/N,N'-methylenebisacrylamide solution. In addition, catalysts are included in the mixture to facilitate polymerization. The polymerization reaction is preferably initiated with ammonium persulfate and N,N,N',N'-tetramethyleneethylenediamine, although other free radical polymerization initiators may be employed as known by those skilled in the art. As an option, to facilitate the incorporation of the matrix into the polymeric gel, the polymerization of the monomer and crosslinking agent can be carried out under high pressure. One means to achieve this is to pressurize the capillary to approximately 5,000 psi during the polymerization. An apparatus for capillary pressurization is described in Bente, III et al., U.S. Pat. No. 4,810,456, which is incorporated herein.

Generally, the concentrations of monomer and crosslinking agent are predetermined according to the porosity of the polymeric gel desired. However, the concentrations of initiator and polymerization catalyst in the reaction mixture are readily determined experimentally. This is done by preparing test solutions containing the desired concentrations of monomer and crosslinking agent, but varying the amount of initiator and polymerization catalyst employed. These test solutions are allowed to polymerize at the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization to be essentially complete at a reasonable time, approximately within one hour.

As stated above, the invention is not limited by the type of gel employed so long as the gel is appropriate for gel electrophoresis and the matrix can be embedded therein during polymerization. For the present invention, agarose based gel can also be used. In the above example, the matrix comprises branched molecules that are crosslinked. Moreover, reactive double bonds are present in the matrix and some of these double bonds will react with functioning groups of the monomer and crosslinking agents that form the polymeric gel. In another embodiment, the matrix, instead of the crosslink network described above, comprises linear hydrophilic molecules covalently bonded to the inner surface of the microcapillaries. For instance, where the microcapillary is made of fused silica, the matrix can be formed by reacting molecules of the general formula R-X, where R represents a hydrophilic linear ligand and X represents a functional group which reacts with the silanol of the glass surface. Appropriate hydrophilic molecules includes methylcellulose, hydroxypropylmethylcellulose, dextrin, agarose, hydroxyethylmethacrylate, methoxyethylmethacrylate, methoxyethoxyethylmethacrylate, and derivatives thereof. See Van Alstine et al., U.S. Pat. No. 4,690,749, issued Sep. 1, 1987.

Figure 5:
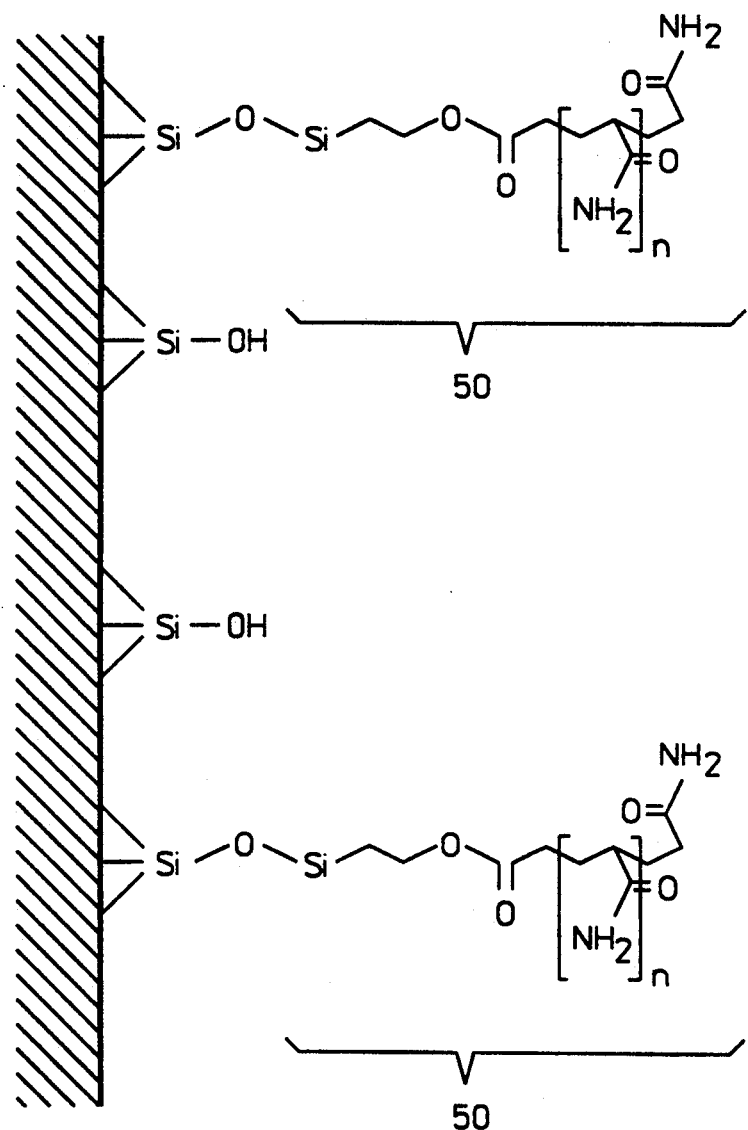
FIG. 5 depicts a matrix comprising linear molecules containing acrylamide polymers.

FIG. 5 depicts a matrix comprising linear molecules 50 containing acrylamide polymers where $n=1$ to 10,000 or more. This matrix is prepared by first forming the modified capillary surface with linear molecules (formed by reacting an acrylic silane with surface silanol groups as described above) as depicted in FIG. 3.

Next, an acrylamide solution is brought into intimate contact with the modified surface. The linear acrylamide polymers are formed upon polymerization of the solution. The matrix as shown in FIG. 5 is not crosslinked and there will be no covalent bonds formed between the matrix molecules and the polymeric gel molecules.

Finally, where the molecules of the matrix are more complex, it may be necessary to employ successive steps to form the matrix. For instance, where long chain molecules are desired, it may be necessary to first modify the inner surface of the capillary by reacting the silanol molecules thereof with a first bifunctional reagent in which one of the functional groups specifically reacts with the silanol group. Thereafter, a second reagent such as a monomer solution is brought into contact with the modified capillary surface and upon polymerization linear polymers are formed which are covalently bonded to first reagents that are attached to the capillary surface. Preferred first reagents include acryloxypropyltrichlorisilane, 3-methacryloxypropyltrimethoxysilane, 3-methacryloxypropyldimethylethoxysilane, vinyltriacetoxysilane, vinyltri ($\beta$-methoxyethoxy)silane, vinyltrichlorosilane, or methaylvinyldichlorosilane. Examples of useful second reagents include N,N'-methylenebisacrylamide, N,N'-(1,2-dihydroxyethylene)-bisacrylamide, N,N'-diallyltartardiamide, N,N'-cystamine-bisacrylamide, or N-acryloyltris(hydroxymethyl)aminomethane.

It is to be understood that while the invention has been described above in conjunction with preferred specific embodiments, the description and examples are intended to illustrate and not limit the scope of the invention, which is defined by the scope of the appended claims.

What is claimed is:

1. A micro column useful for gel capillary electrophoresis comprising:
    a tube having a bore with an inner surface;
    linear reagent molecules, each having a first end and a second end, wherein the first end is covalently bonded to the inner surface;
    hydrophilic molecules each covalently bonded to the second end of a respective reagent molecule and forming a matrix; and
    crosslinked polymeric gel filling the bore wherein at least a portion of the gel is embedded in the matrix.

2. The microcolumn as defined in claim 1 wherein some of the hydrophilic molecules forming the matrix are branched and crosslinked.

3. The microcolumn as defined in claim 2 wherein some of the hydrophilic molecules that form the matrix are bonded to polymeric gel molecules.

4. The micro column as defined in claim 3 wherein the reagent molecules are selected from the group consisting of acryloxypropyltrichlorisilane, 3-methacryloxypropyltrimethoxysilane, 3-methacryloxypropyldimethylethoxysilane, vinyltriacetoxysilane, vinyltri($\beta$-methoxyethoxy)silane, vinyltrichlorosilane, and methaylvinyldichlorosilane.

5. The microcolumn as defined in claim 4 wherein the polymeric gel comprises a copolymer of acrylamide and at least one crosslinking agent.

6. The microcolumn as defined in claim 5 wherein the crosslinking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

7. A method of preparing an electrophoretic gel column including a gel substantially free of shrinkage defects, the method comprising the steps of:
    providing a microcolumn having a bore;
    bonding hydrophilic molecules to at least a portion of the bore to form a matrix thereat;
    contacting the matrix with a monomer solution; and
    polymerizing the monomer solution to form a polymeric gel formed with the matrix embedded therein.

8. The method of preparing an electrophoretic gel column as defined in claim 7 further comprising the step of treating the microcolumn with a first crosslinking agent to crosslink a substantial number of the hydrophilic molecules.

9. The method of preparing an electrophoretic gel column as defined in claim 8 further comprising the step of adding a second crosslinking agent to the monomer solution so that the polymeric gel formed is crosslinked.

10. The method of preparing an electrophoretic gel column as defined in claim 9 further comprising the step of:
    adding a catalyst to the monomer solution prior to polymerization.

11. A method of preparing an electrophoretic gel column including a gel substantially free of shrinkage defects, the method comprising the steps of:
    providing a micro column having a bore;
    treating the micro column bore with a solution containing a reagent that is capable of reacting with and bonding to hydrophilic molecules, to cause the reagent to be covalently bonded to at least a portion of the bore surface;
    contacting reagent molecules that are bonded to the bore surface with hydrophilic molecules to cause the reagent molecules to be covalently bonded with the hydrophilic molecules and forming a matrix adjacent thereto;
    contacting the matrix with a monomer solution; and
    polymerizing the monomer solution in contact with the matrix to embed a polymeric gel formed therefrom in the matrix.

12. The method of preparing an electrophoretic gel column as defined in claim 11 further comprising the step of adding a crosslinking agent to the monomer solution so that the polymeric gel formed is crosslinked.

13. The method of preparing an electrophoretic gel column as defined in claim 12 wherein the monomer is acrylamide and the reagent is selected from the group consisting of acryloxypropyltrichlorisilane, 3-methacryloxypropyltrimethoxysilane, 3-methacryloxypropyldimethylethoxysilane, vinyltriacetoxysilane, vinyltri($\beta$-methoxyethoxy)silane, vinyltrichlorosilane, and methaylvinyldichlorosilane.

14. The method of preparing an electrophoretic gel column as defined in claim 11 further comprising the step of adding a crosslinking agent to the monomer solution so that the polymeric gel formed is crosslinked.

15. The method of preparing an electrophoretic gel column as defined in claim 14 further comprising the step of:
    adding a catalyst to the monomer solution prior to polymerization.

16. The method of preparing an electrophoretic gel column as defined in claim 12 wherein said reagent is a first reagent that includes functional groups $R_1$ and $R_2$, wherein $R_1$ is capable of reacting with and bonding to bore surface molecules and $R_2$ is capable of reacting with and bonding to hydrophilic molecules, to cause first reagent molecules to be covalently bonded to at least a portion of the bore surface and wherein the hydrophilic molecules are formed by polymerizing a solution containing a second reagent.

17. The method of preparing an electrophoretic gel column as defined in claim 16 further comprising the step of adding a crosslinking agent to the monomer solution so that the polymeric gel formed is crosslinked.

18. The method of preparing an electrophoretic gel column as defined in claim 17 wherein the first reagent is selected from the group consisting of acryloxypropyltrichlorisilane, 3-methacryloxypropyltrimethoxysilane, 3-methacryloxypropyldimethylethoxysilane, vinyltriacetoxysilane, vinyltri($\beta$-methoxyethoxy)silane, vinyltrichlorosilane, and methylvinyldichlorosilane, and the second reagent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

19. The method of preparing an electrophoretic gel column as defined in claim 18 wherein the monomer is acrylamide.

20. The method of preparing an electrophoretic gel column as defined in claim 19 further comprising the step of removing unreacted first and second reagent molecules before the step of contacting the matrix with the monomer solution.

21. The method of preparing an electrophoretic gel column as defined in claim 20 wherein the hydrophilic polymer molecules are branched and crosslinked.

22. A method of preparing an electrophoretic gel column as defined in claim 21 wherein the crosslinking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

23. The method of preparing an electrophoretic gel column as defined claim 11 wherein said monomer solution is a first monomer solution and said reagent is a first reagent including functional groups $R_1$ and $R_2$ wherein $R_1$ is capable of reacting with and bonding to the bore surface and $R_2$ is capable of reacting with and boning to first monomers, to cause the reagent molecules to be covalently bonded to at least a portion of the bore surface; said method further comprising the steps of:
  contacting the first reagent molecules that are bonded to the microcolumn bore surface with a solution containing a second reagent having functional groups $R_3$ and $R_4$ wherein both $R_3$ and $R_4$ are capable of reacting with $R_2$ and wherein $R_3$ of one second reagent molecule can react with a $R_4$ of another second reagent molecule;
  and polymerizing the second reagent solution to form a matrix of hydrophilic molecules.

24. The method of preparing an electrophoretic gel column as defined in claim 23 wherein the first reagent is selected from the group consisting of acryloxypropyltrichlorisilane, 3-methacryloxypropyltrimethoxysilane, 3-methacryloxypropyl-dimethylethoxysilane, vinytriacetoxysilane, vinltri($\beta$-methoxyethoxy)silane, vinyltrichlorosilane, and methaylvinyldichlorosilane.

25. The method of preparing an electrophoretic gel column as defined in claim 24 wherein the hydrophilic polymer molecules are branched and crosslinked.

26. The method of preparing an electrophoretic gel column as defined in claim 25 wherein the monomer is acrylamide.

27. The method of preparing an electrophoretic gel column as defined in claim 26 further comprising the step of adding a crosslinking agent to the monomer solution.

28. The method of preparing an electrophoretic gel column as defined in claim 27 wherein the crosslinking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

29. The method of preparing an electrophoretic gel column as defined in claim 28 wherein the step of polymerizing the second monomer is accomplished with the use of a catalyst.

30. The method of preparing an electrophoretic gel column as defined in claim 29 further comprising the step of applying pressure to the monomer solution during its polymerization.

31. The method of preparing an electrophoretic gel column as defined in claim 30 wherein the step of applying pressure is accomplished by subjecting the monomer solution to pressure of approximately 5,000 psi.

32. A method of preparing an electrophoretic gel column including a gel substantially free of shrinkage defects, the method comprising the steps of:
  providing a microcolumn having a bore;
  treating the microcolumn bore with a solution containing a reagent having functional groups $R_1$ and $R_2$ wherein $R_1$ is capable of reacting with and bonding to bore surface molecules and $R_2$ is capable of reacting with and bonding to first monomers, to cause the reagent molecules to be covalently bonded to at least a portion of the bore surface;
  contacting the reagent molecules that are bonded to the bore surface with a first monomer solution;
  polymerization the first monomer solution to form polymer molecules that are bonded to the reagent molecules, wherein the polymer molecules and the reagent molecules bonded thereto form a matrix;
  contacting the matrix with a second monomer solution; and
  polymerizing the second monomer solution in contact with the matrix to embed a polymeric gel formed therefrom in the matrix.

33. The method of preparing an electrophoretic gel column as defined in claim 32 further comprising the step of adding a crosslinking agent to the second monomer solution so that the polymeric gel formed is crosslinked.

34. The method of preparing an electrophoretic gel column as defined in claim 33 wherein the reagent is selected from the group consisting of acryloxypropyltrichlorisilane, 3-methacryloxypropyltrimethoxysilane, 3-methacryloxypropyldimethylethoxysilane, vinyltriacetoxysilane, vinyltri ($\beta$-methoxyethoxy)silane, vinyltrichlorosilane, and methaylvinyldichlorosilane and the first monomer is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

35. The method of preparing an electrophoretic gel column as defined in claim 34 wherein the second monomer is acrylamide.

36. The method of preparing an electrophoretic gel column as defined in claim 35 further comprising the step of removing unreacted reagent before the step of contacting the reagent molecules with the first monomer solution.

37. The method of preparing an electrophoretic gel column as defined in claim 36 wherein the first polymerization step causes the formation of hydrophilic polymer molecules that are bonded to the bore surface.

38. The method of preparing an electrophoretic gel column as defined in claim 36 wherein the hydrophilic polymer molecules are branched and crosslinked.

39. A method of preparing an electrophoretic gel column as defined in claim 38 wherein the cross-linking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

40. A method of preparing an electrophoretic gel column including a gel substantially free of shrinkage defects, the method comprising the steps of:
providing a microcolumn having a bore;
treating the microcolumn bore surface with a solution containing a first reagent having functional groups $R_1$ and $R_2$ wherein $R_1$ is capable of reacting with and bonding to the microcolumn bore surface, to cause covalent bonding of said first reagent to at least a portion of the bore surface;
contacting the first reagent molecules that are bonded to the microcolumn bore surface with a solution containing a second reagent having functional groups $R_3$ and $R_4$ wherein both $R_3$ and $R_4$ are capable of reacting with $R_2$ and wherein $R_3$ of one second reagent molecule can react with a $R_4$ of another second reagent molecule,
polymerizing the second reagent solution to form a matrix of hydrophilic molecules;
contacting the matrix with a monomer solution; and
polymerizing the monomer solution in contact with the matrix to embed a polymeric gel formed therefrom in the matrix.

41. The method of preparing an electrophoretic gel column as defined in claim 40 wherein the first reagent is selected from the group consisting of acryloxypropyltrichlorisilane, 3-methacryloxypropyltrimethoxysilane, 3-methacryloxypropyldimethylethoxysilane, vinyltriacetoxysilane, vinltri (β-methoxyethoxy)silane, silane, vinyltrichlorosilane, and methaylvinyldichlorosilane.

42. The method of preparing an electrophoretic gel column as defined in claim 41 wherein the hydrophilic polymer molecules are branched and crosslinked.

43. The method of preparing an electrophoretic gel column as defined in claim 42 wherein the monomer is acrylamide.

44. The method of preparing an electrophoretic gel column as defined in claim 43 further comprising the step of adding a crosslinking agent to the monomer solution.

45. The method of preparing an electrophoretic gel column as defined in claim 44 wherein the crosslinking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

46. The method of preparing an electrophoretic gel column as defined in claim 45 wherein the step of polymerizing the monomer is accomplished with the use of a catalyst.

47. The method of preparing an electrophoretic gel column as defined in claim 46 further comprising the step of applying pressure to the monomer solution during its polymerization.

48. The method of preparing an electrophoretic gel column as defined in claim 47 wherein the step of applying pressure is accomplished by subjecting the monomer solution to pressure of approximately 5,000 psi.

* * * * *